United States Patent [19]

McCord et al.

[11] E Patent Number: Re. 33,518

[45] Reissued Date of Patent: Jan. 15, 1991

[54] PRESSURE TRANSDUCER ASSEMBLY

[75] Inventors: Kenneth R. McCord, Yorba Linda; James K. Bullock, Burbank; Keith Gilroy, Upland; Henrick K. Gille, Monrovia; Edward J. Arkans, Sunland; Paul Anderson, Tujunga, all of Calif.

[73] Assignee: Baxter International, Inc., Deerfield, Ill.

[21] Appl. No.: 95,416

[22] Filed: Sep. 10, 1987

Related U.S. Patent Documents

Reissue of:

[64] Patent No.: 4,539,998
Issued: Sep. 10, 1985
Appl. No.: 489,900
Filed: Apr. 29, 1983

[51] Int. Cl.[5] ..... A61B 5/215

[52] U.S. Cl. ..... 128/675; 128/748; 73/706; 73/708

[58] Field of Search ..... 128/672–675, 128/748; 73/706, 708, 717, 721, 723, 727

[56] References Cited

U.S. PATENT DOCUMENTS

| | | | |
|---|---|---|---|
| 2,747,407 | 5/1956 | Knoll . | |
| 2,959,056 | 11/1960 | Traite et al. . | |
| 3,550,583 | 12/1970 | Chiku et al. . | |
| 3,608,370 | 9/1971 | Vollenweider et al. . | |
| 3,713,341 | 1/1973 | Madsen et al. | 128/675 X |
| 3,939,823 | 2/1976 | Kaye et al. . | |
| 4,003,141 | 1/1977 | LeRoy . | |
| 4,023,562 | 5/1977 | Hynecek et al. | 128/748 |
| 4,028,945 | 6/1977 | Bergamini . | |
| 4,072,056 | 2/1978 | Lee | 128/675 X |
| 4,077,882 | 3/1978 | Gangemi | 128/675 X |
| 4,191,193 | 3/1980 | Seo . | |
| 4,198,868 | 4/1980 | Runyan . | |
| 4,226,124 | 10/1980 | Kerstein | 128/675 X |
| 4,227,420 | 10/1980 | Lamadrid | 73/706 X |
| 4,236,880 | 12/1980 | Archibald . | |
| 4,237,935 | 12/1980 | Delmonte et al. | 128/675 X |
| 4,252,126 | 2/1981 | Mandl | 128/675 X |
| 4,274,423 | 6/1981 | Mizuno et al. . | |
| 4,291,293 | 9/1981 | Yamada et al. . | |
| 4,314,480 | 2/1982 | Becker | 128/675 X |
| 4,317,126 | 2/1982 | Gragg, Jr. . | |
| 4,320,664 | 3/1982 | Rehn et al. . | |
| 4,370,890 | 2/1983 | Frick | 73/708 X |
| 4,382,247 | 5/1983 | Stecher et al. . | |
| 4,398,542 | 8/1983 | Cunningham et al. | 128/675 |
| 4,400,682 | 8/1983 | Ishibashi . | |
| 4,465,075 | 8/1984 | Swartz | 73/708 X |

FOREIGN PATENT DOCUMENTS

| | | |
|---|---|---|
| 2925880 | 1/1981 | Fed. Rep. of Germany . |
| 1212264 | 3/1960 | France . |
| 1583433 | 10/1969 | France . |
| 2125991 | 9/1972 | France . |
| 0022933 | 2/1983 | Japan . |
| 0168930 | 10/1983 | Japan . |
| 0168931 | 10/1983 | Japan . |

OTHER PUBLICATIONS

Cobe Disposable Transducer System, Dec., 1981.
"MPX Pressure Transducers", Motorola Inc.

*Primary Examiner*—Angela D. Sykes
*Attorney, Agent, or Firm*—Gordon L. Peterson

[57] ABSTRACT

A pressure transducer assembly is disclosed for directly monitoring pressure in a fluid which flows through the assembly. The assembly includes a housing defining a chamber therewithin and having an inlet port and an outlet port in fluid-flow communication with the chamber. An electrically insulated body element is sealed within the chamber dividing the chamber into a first chamber and a second chamber. The first chamber is in fluid-flow communication with the inlet and outlet ports. The second chamber is separated from the first chamber by a fluid-tight seal such that any fluid present in the first chamber cannot enter the second chamber. A pressure transducer sensor is secured in the insulated body and exposed to the first chamber such that the sensor can determine the pressure in a fluid in the first chamber and convert the pressure into electric impulses. The sensor is separated from the fluid in the first chamber by an insulating medium across which fluid pressure can be determined. Connected to the sensor are electrical conductors which extend through the insulated body and into the second chamber. The second chamber provides an engagement site for an electrical connector which can interconnect with the electrical conductors and provide an electrical path through which the electric impulses generated by the sensor can be transferred to a monitor.

58 Claims, 3 Drawing Sheets

PRESSURE TRANSDUCER ASSEMBLY

Matter enclosed in heavy brackets [ ] appears in the original patent but forms no part of this reissue specification; matter printed in italics indicates the additions made by reissue.

BACKGROUND OF THE INVENTION

The pressure transducer assembly herein can be used in any fluid line for which the fluid pressure within the line is to be determined. The pressure transducer assembly herein has particular utility for the invasive monitoring of blood pressure. In a particular application, the pressure transducer assembly provides a disposable pressure transducer assembly which can be used for a single patient use and then discarded.

Invasive blood pressure monitoring as a system which provides an accurate method for monitoring the blood pressure of a patient. Frequently, invasive blood pressure monitoring is performed for critically infirmed patients. Invasive blood pressure monitoring is also performed during critical surgeries and on patients in intensive care units and critical care units. Invasive blood pressure monitoring is gaining acceptance in conjunction with the care and treatment of cardiac [pateints] *patients* and for providing a technique for the constant, accurate determination of blood pressures for such patients. Invasive blood pressure monitoring is used with cardiac catheterization to provide bedside cardiac and blood pressure monitoring. In invasive blood pressure monitoring, a catheter is inserted into a patient's circulatory system with the end of the catheter having an opening which is open to the blood stream. In many instances, the catheter is inserted into the circulatory system such that the proximal end of the catheter reaches the heart in order to provide monitoring of atrial and venous pressures. An I.V. set is generally attached to the distal end of the catheter protruding from the patient. An I.V. solution bag in the I.V. set assembly contains a solution which is permitted to flow through the catheter and into the patient. The I.V. solution extending through the catheter and into the patient provides a fluid pathway for pressure in the patient's circulatory system. By positioning a pressure transducer along the fluid pathway, the blood pressure in the patient's circulatory system can be monitored. Generally, such a pressure transducer consists of a dome which functions as a reservoir for the I.V. fluid. The dome includes a resilient diaphragm which attaches to an electrical transducer. The transducer senses pressure fluctuations in the diaphragm and converts such pressure fluctuations into electrical impulses which are transmitted to a monitor.

The pressure transducers that are currently used in invasive monitoring systems are relatively expensive and are generally constructed to be reusable following sterilization. Some pressure transducers can be reused as they are not in direct contact with the fluid being administered but rather are adapted to be connected to fluid reservoir domes which can be either disposable or reusable.

It would be desirable to provide a pressure transducer in a single integrated assembly which can provide an accurate monitoring of fluid pressure while being inexpensive and disposable. It would also be desirable to provide such a pressure transducer such that the pressure in the fluid pathway is determined and converted to electrical impulses such that the transducer need only be electrically connected to a readout monitor or display unit for such determined pressures.

SUMMARY OF THE INVENTION

The invention herein is directed to a pressure transducer assembly for directly monitoring pressure in a fluid which flows through the assembly. The assembly includes a housing defining a chamber therewithin and having an inlet port and an outlet port in fluid-flow communication with the chamber. An electrically insulated body element is sealed within the chamber dividing the chamber into a first chamber and a second chamber within the housing. The first chamber is in fluid-flow communication with the inlet and outlet ports. The second chamber is separated from the first chamber by a fluid-tight seal such that any fluid present in the first chamber cannot enter the second chamber. A pressure transducer sensor is secured in the insulated body and exposed to the first chamber such that the pressure transducer sensor can determine the fluid pressure in a fluid in the first chamber and convert the sensed fluid pressure into electric impulses. The pressure transducer sensor is separated from the fluid in the first chamber by an insulating medium across which fluid pressure can be determined but electrical current cross. Connected to the pressure transducer sensor are electrical conductors which extend through the insulated body and into the second chamber. The second chamber provides an engagement site for an electrical connector which can interconnect with the electrical conductors and provide an electrical path through which the electric impulses generated by the pressure transducer sensor can be transferred to a monitor for monitoring the fluid pressure within the fluid in the first chamber.

DETAILED DESCRIPTION

Figure 6:
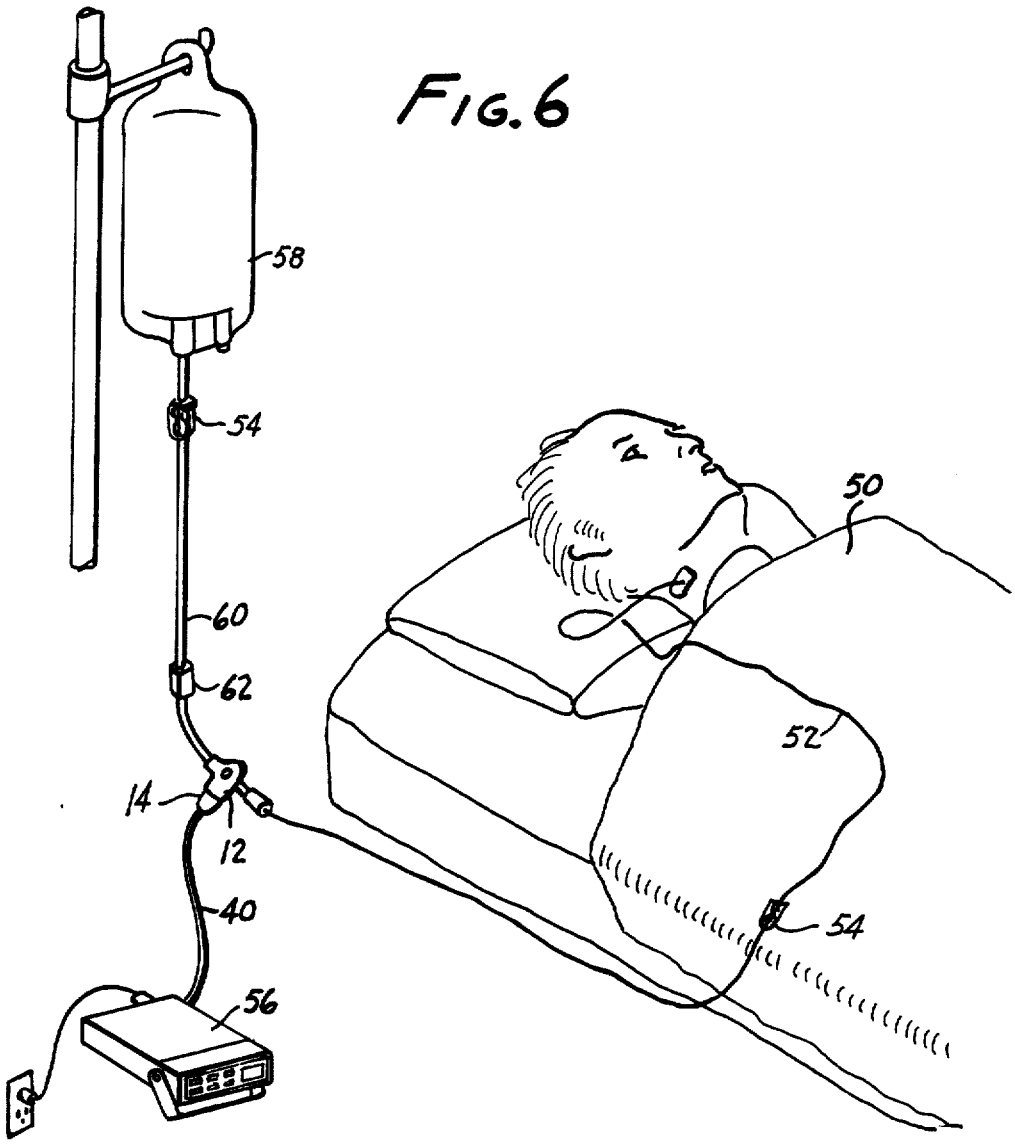
FIG. 6 is a schematic representation of a pressure transducer assembly illustrating its utility in a technique for the invasive monitoring of blood pressure.

The pressure transducer assembly herein will be described with regard to the accompanying drawings wherein the overall assembly and utility for the assembly is illustrated in FIG. 6. FIG. 6 schematically represents the use of the pressure transducer assembly herein for invasive blood pressure monitoring.

Figure 1:
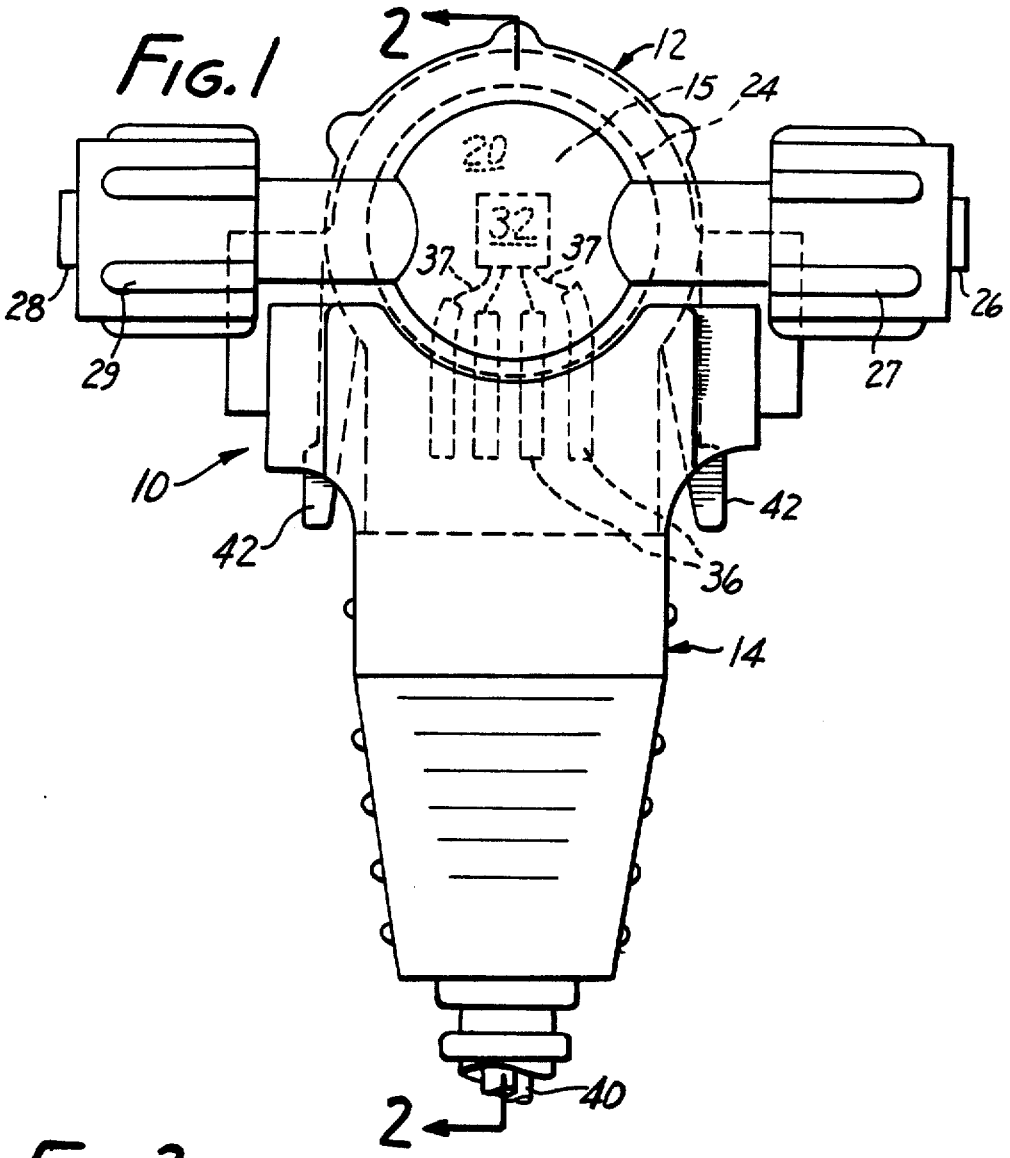
FIG. 1 is a top plan view of the pressure transducer assembly herein connected to an electrical connector which can form a part of the assembly herein.

In particular, the invention herein resides in the pressure transducer housing assembly 12 shown in FIG. 1. With regard to FIG. 1, the pressure transducer assembly 10 is shown in part by the pressure transducer housing assembly 12 which is connected to an electrical connector assembly 14. The electrical connector assembly is structured to enable electrical connection with the pressure transducer assembly so as to provide power to the pressure transducer assembly and to provide a route for electrical impulses generated by the pressure transducer assembly.

The pressure transducer housing assembly comprises a housing 16 which defines a chamber 15 therein. The chamber 15 is divided into a first chamber 20 and a second chamber 22 by an insulated body 24 which is sealed to the housing within the chamber 15. The insulated body 24 is nonconductive of electricity and is constructed of a suitable material that is compatible with the material of the housing, which is biocompatible with the human physiology, and which will not react with the fluid being administered to a patient through the pressure transducer assembly. The material of the insulated body is selected from a material which can be sealed to the housing to provide a fluid-tight seal between the first and second chambers. The housing can be constructed of any suitable material which is biocompatible with the human physiology including materials such as polycarbonate, polypropylene, polyethylene, polysulfone and the like. A suitable material for the insulated body member is polysulfone. The insulated body member can be sonically welded to seal the body member within the chamber 15 and to form and separate the first chamber 20 and the second chamber 22. Constructing the housing and presure transducer assembly of the plastic materials described makes the assembly disposable so that it can be discarded after a single patient use. Such materials are inexpensive and easy to mold, such as by injection molding in large volumes.

The first chamber 21 is in fluid-flow communication with an inlet port 26 provided on the housing. The first chamber is also in fluid-flow communication with an outlet port 28 provided on the housing. The inlet and outlet ports can be hollow, cylindrically extending portions of the housing which project from the housing to enable the affixing of tubing (shown in FIG. 6) to the housing. Preferably, the inlet and outlet ports are axially aligned to provide a substantially unimpeded flow path through the housing. The inlet port, outlet port and first chamber provide a fluid-flow pathway through which fluid can be administered to a patient while simultaneously permitting the monitoring of pressure waves along the fluid pathway. The inlet port can be provided with a rotating adapter 27 or other similar attachment means such as Linden fittings, Luer fittings and the like whereby a catheter or tubing can be attached to the housing in a fluid-tight seal. Similarly, the outlet port can be provided with a rotating adapter 29 to connect a catheter or tubing to the outlet side of the housing.

The housing can include a dome 30 which is a portion of the housing that is structured in a dome which extends over the first chamber. The dome is preferably constructed of a clear material such that any fluid within the first chamber can be observed. The dome functions as a clear lens which permits the observation of the fluid and any bubbles which can be present in the fluid. The dome can also function to trap, or momentarily trap, any air bubbles which can be present in the fluid. The presence of air bubbles is undesirable as it can provide erroneous pressure readings and it is undesirable to introduce air bubbles to the patient.

Positioned within the first chamber is a pressure sensor such as a silicon pressure sensor 32. In the preferred embodiment, the pressure sensor is positioned in a depression on the insulated body as can be readily seen from the cross-sectional view of FIG. 2. The silicon pressure sensor is a pressure transducer which is capable of sensing or determining a pressure in any fluid present in the first chamber and converting such pressure to an electric impulse. Preferably, the pressure transducer is a monolithic silicon pressure sensor employing a four-terminal resistive element formed in a thin monocrystalline silicon diaphragm. Acceptable silicon pressure sensors are commercially available from Motorola, Inc., Sensors which can be used in the pressure transducer assembly herein include the sensors that are disclosed in U.S. Pat. No. 4,317,126 assigned to Motorola, Inc., the entire disclosure of which is incorporated herein by this reference. In addition to the sensors disclosed in the U.S. Pat. No. 4,317,126 patent, a particularly preferred silicon pressure sensor is a sensor which includes a temperature compensation circuit for compensating the sensed pressure in the fluid based upon the temperature of the fluid and correcting such sensed pressure. Such a silicon pressure sensor is commercially available from Motorola, Inc. as SPX-1001D pressure sensors.

Figure 2:
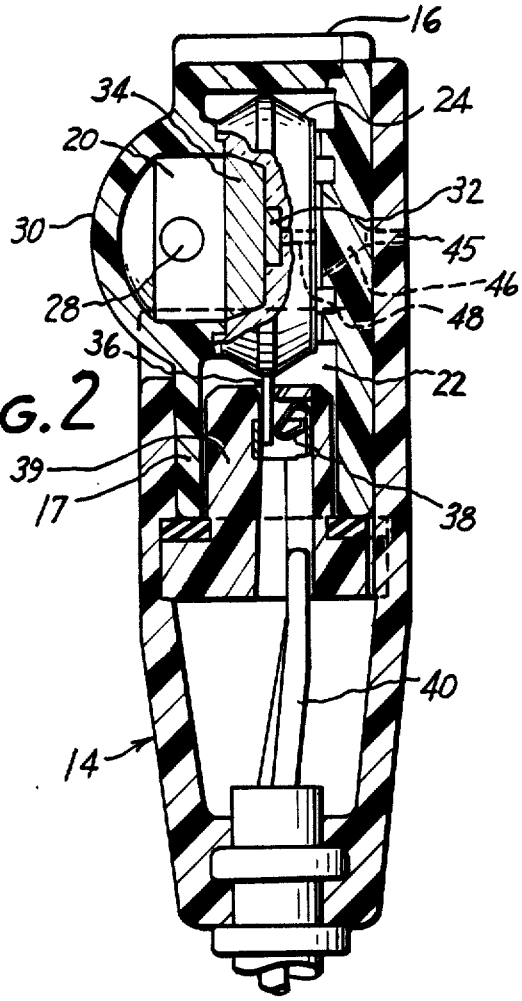
FIG. 2 is a lateral cross-sectional view of the embodiment shown in FIG. 1 taken along lines 2—2.

Covering the pressure sensor 32, as can be more readily seen in the cross-sectional view shown in FIG. 2, is an insulating medium 34. Insulating as used with regard to the insulating medium refers to the nonconductance of electricity. The insulating medium 34 extends over and completely covers the silicon pressure sensor such that there is no electrical connection or electrical pathway between fluid in the first chamber and the silicon pressure sensor. As seen in FIG. 2, the term "covers" is used to mean that the insulating medium and silicon pressure sensor are mechanically contiguous. The insulating medium 34 comprises a material that is sufficiently fluid-like that it transmits the pressure in the fluid to the sensor. The insulating medium is also preferably biocompatible as it is in contact with the fluid being administered to the patient. A particularly preferred insulating medium is a silicone polymer, such as a methyl silicone elastomer. Such an insulating medium prevents electrical shock to the patient through the fluid as any electrical current to the silicon pressure sensor is insulated from the fluid in the first chamber by the insulating medium.

In order for the silicon pressure sensor to accurately measure the pressure of the fluid in the first chamber, the silicon pressure sensor is preferably vented to the atmosphere. The venting of the silicon pressure sensor to the atmosphere is accomplished by providing a first aperture 45 in the base of the electrical connector which coincides and aligns with a second aperture 46 in the housing. The second aperture in the housing opens into the second chamber and coincides and aligns with a third aperture 48 in the insulated body. The third aperture 48 in the insulated body opens to the lower side of the silicon pressure sensor and thereby provides a direct pathway to the atmosphere for the silicon pressure sensor.

A series of electrical pins 36 extend through the insulated body 24 into the first chamber and are in electrical contact with the silicon pressure sensor 32 through suitable circuits 37. The portion of the pins 36 which extend into the first chamber are completely imbedded within the insulating medium 34 and thereby physically separated from fluid in the first chamber by the insulating medium. The electrical pins extend through the insulated body and into the second chamber of the housing of the pressure transducer assembly. The electrical pins extend from the insulated body to provide a male electrical plug which can be inserted into a corresponding female electrical plug on the electrical connector assembly 14 to provide electrical contact between the pressure transducer housing assembly and the electrical connector assembly.

Figure 3:
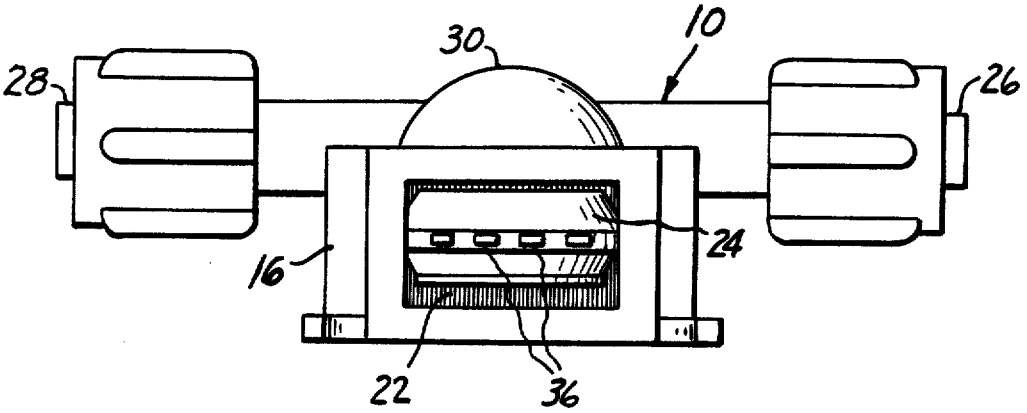
FIG. 3 is a side elevational view of the pressure transducer assembly shown in FIG. 1.

In the preferred embodiment, the second chamber is open and provides a receptor site for the electrical connector assembly. That is, at least a portion of the electrical connector assembly can be inserted into the second chamber to mate with the electrical pins. The view shown in FIG. 3 of the drawing shows a view of the pressure transducer housing assembly looking into the open second chamber 22 wherein the insulated body 24 can be seen with the extending electrical pins 36. In other embodiments, the electrical pins can also extend through the sidewall of the housing to enable connection to an electrical connector assembly.

Figure 4:
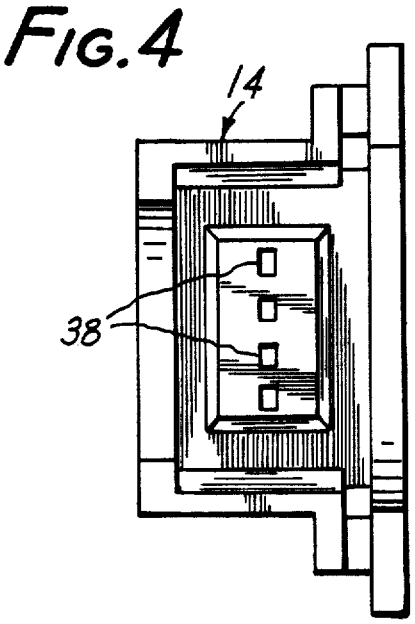
FIG. 4 is an end elevational view of the electrical connector which connects to the pressure transducer housing assembly.
Figure 5:
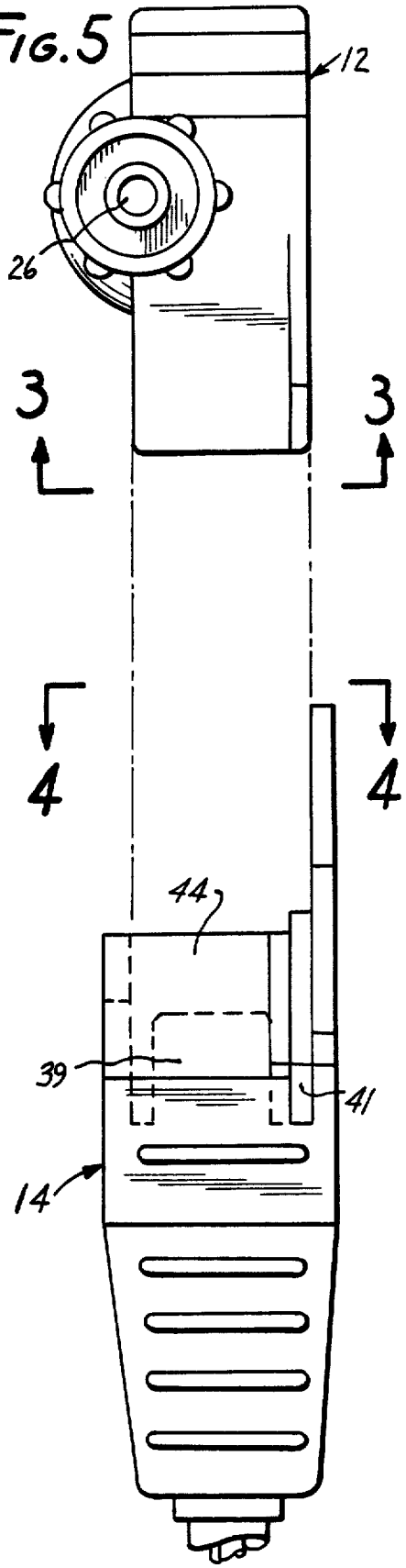
FIG. 5 is an exploded view of the pressure transducer housing assembly and the electrical connector assembly.

The electrical connector assembly can be mated to the pressure transducer housing assembly. The electrical connector assembly includes electrical plug receptors 38 which receive the electrical pins 36. The electrical plug receptors are connected through suitable wiring 40 which can carry the electrical impulses generated by the silicon pressure sensor to a suitable display unit or monitor as is shown in FIG. 6. Such wiring can also provide power to the pressure transducer assembly. An end view of the electrical connector assembly 14 is illustrated in FIG. 4. The mating of the pressure transducer housing assembly and the electrical connector assembly is shown in an exploded view in FIG. 5. The electrical connector assembly can include a cavity 44 into which a portion 17 of the housing 16 of the pressure transducer housing assembly can be inserted to mate the electrical pins 36 and electrical plug receptors 38. The electrical connector assembly can include a projecting portion 39 which can insert into the open second chamber of the housing. Such an arrangement provides a relatively snug fit between the pressure transducer housing assembly and the electrical connector assembly to prevent inadvertent separation of the assemblies. In a preferred embodiment of the invention, the pressure transducer housing assembly and the housing 16 thereof can be provided with resilient snap-fitting projections such as the resilient arm portions 42 which can be inserted into and snap-fittingly engage suitable apertures 41 in the body of the electrical connector assembly 14.

The electrical connector assembly provides an electrical conduit between the pressure transducer housing assembly and a display unit. The electrical connector assembly includes the assembly 14 and the associated wiring 40 which leads from the electrical connector assembly to a display unit.

The utility of the pressure transducer assembly herein is schematically illustrated in FIG. 6. In FIG. 6, a patient 50 is catheterized with a catheter which extends into the circulatory system. The catheter is connected at about the exit site from the patient of flexible tubing 52 along which can be positioned a clamp 54 for occluding fluid flow through the tubing. The tubing 52 is connected to the pressure transducer housing assembly 12 at the outlet port. As can be seen by one having skill in the art, the housing of the pressure transducer housing assembly can be positioned in any manner with regard to inlet and outlet flow of fluid as the direction of flow of any fluid through the housing does not influence the pressure reading by the silicon pressure sensor. The terms inlet and outlet, as used herein, are merely arbitrarily assigned to the two ports on the housing to facilitate the description of utility.

The inlet port of the housing is connected through suitable flexible tubing 60 to a source of an I.V. solution such as an I.V. bag and drip chamber 58. A clamp 54 and a fluid-flow restriction device 62 can be positioned along the flexible tubing leading to the pressure transducer housing assembly 12.

The electrical connector assembly 14 is interconnected to the pressure transducer housing assembly. The wiring 40 extending therefrom can be connected to a suitable display unit or monitor 56 can be powered by batteries or by normal alternating current.

In operation, prior to connecting the flexible tubing 52 to the catheter which has been inserted in the patient, fluid from the I.V. bag is permitted to flow through the tubing 60, pressure transducer housing assembly 12, and flexible tubing 52. The connection between the flexible tubing 52 and catheter is then made so as to prevent the formation or inclusion of entrapped air along the fluid-flow path. After connecting the tubing 52 to the catheter, a complete fluid-flow path is [obtined] *obtained* and with the communication of the fluid in the pressure transducer assembly and the patient's circulatory system, any pressure within the circulatory system is correspondingly observed in the fluid present in the first chamber of the pressure transducer assembly. The silicon pressure sensor thereby observes the pressure in the fluid and transforms such sensed pressure into electrical impulses which flow along the wiring 40 to the display unit 56 wherein the pressure readings are displayed for the benefit of the attendant.

We claim:

1. A pressure transducer assembly for monitoring pressure in a fluid comprising:

a housing defining a chamber and having an inlet port and an outlet port in fluid-flow communication with the chamber;

an insulated body sealed within the chamber which forms separate first and second chambers within the housing with the first chamber in fluid-flow communication with the inlet port and outlet port;

a pressure transducer means secured in the insulated body and exposed to the first chamber for determining and converting fluid pressure within a fluid in the first chamber into electrical impulses;

a fluid pressure responsive media covering the pressure transducer means which is electrically nonconductive and which separates the pressure transducer means from any fluid present in the first chamber;

electrical conducting means connected to the pressure transducer means and extending through the insulated body and into the second chamber for providing electrical connection between the pressure transducer means in the first chamber and the second chamber; and engagement means on the housing for providing a connection locus on the housing for electrical wiring which can be interconnected with the electrical conducting means.

2. A pressure transducer assembly as required in claim 1 wherein the fluid pressure responsive media comprises silicone elastomer.

3. A pressure transducer assembly as recited in claim 1 further comprising tubing connecting means on the inlet and outlet ports for connecting tubing to the housing.

4. A pressure transducer assembly as recited in claim 1 wherein the electrical conducting means comprises a plurality of electrical conducting metal pins electrically interconnected to the pressure transducer means to transfer power to the pressure transducer means and to transfer away electrical impulse signals corresponding to determined pressures.

5. A pressure transducer assembly as recited in claim 1 wherein the insulated body sealed within the chamber comprises a polysulfone body.

6. A pressure transducer assembly as recited in claim 1 wherein the pressure transducer means comprises a silicon pressure transducer with a single piezoresistive element.

7. A pressure transducer assembly as recited in claim 6 wherein the pressure transducer means comprises a monolithic silicon pressure sensor employing a four-terminal resistive element formed in a monocrystalline silicon diaphragm.

8. A pressure transducer assembly as recited in claim 1 wherein the pressure transducer means monitors fluid pressure within the first chamber in the range from about −50 mmHg to +300 mmHg.

9. A pressure transducer assembly as recited in claim 1 further comprising a clear lens means on the housing extending over the first chamber for viewing fluid and bubbles in the fluid within the first chamber.

10. A pressure transducer assembly as recited in claim 9 wherein the clear lens means comprises a clear dome portion on the housing extending over at least a portion of the first chamber.

11. A pressure transducer assembly as recited in claim 1 wherein the housing comprises a biocompatible polymeric material.

12. A pressure transducer assembly as recited in claim 11 wherein the biocompatible polymeric material is selected from the group consisting of polycarbonate, polypropylene, polyethylene and polysulfone.

13. A pressure transducer assembly as recited in claim 1 further comprising vent means on the housing and on the insulated body for providing exposure to the atmosphere for the pressure transducer means.

14. A pressure transducer assembly as recited in claim 13 wherein the vent means comprises an opening extending through the housing into the second chamber and aligned with an opening extending through the insulated body and leading to the pressure transducer means.

15. A pressure transducer assembly as recited in claim 1 wherein the engagement means comprises a resilient, snap-fitting means for connecting electrical wiring to the assembly.

16. A pressure transducer assembly as recited in claim 15 wherein the resilient, snap-fitting means comprises an opening into the second chamber for receiving an electric wiring connector and at least one resilient portion of the housing for engaging an electric wiring connector and which is deformable for releasing such an electric wiring connector.

17. A pressure transducer assembly as recited in claim 1 further comprising a wiring connector means which engages the electrical conducting means in the second chamber for transmitting electric impulses generated by the pressure transducer means along electrical wiring to a monitoring means for displaying fluid pressure in fluid in the first chamber.

18. A pressure transducer assembly as recited in claim 17 wherein the electrical conducting means comprises electrical pins extending into the second chamber and the wiring connector means comprises a body having electrical pins engaging terminals and which slides into the second chamber and which [engaging] *engages* the electrical pins.

19. A pressure transducer assembly as recited in claim 1 wherein the pressure transducer means includes a temperature compensation circuit means for determining fluid pressure at the [second] *sensed* temperature of a fluid in the first chamber.

20. A pressure transducer assembly as recited in claim 1 wherein the inlet port and outlet port are axially aligned.

21. A disposable pressure transducer assembly for use in the invasive monitoring of blood pressure, the assembly comprising:

a housing defining a chamber therewithin and having an inlet port and an outlet port in fluid-flow communication with the chamber.

an electrically insulated intervening wall in the chamber separating the chamber into a first chamber and a second chamber wherein the first chamber is in fluid-flow communication with the inlet port and outlet port and the second chamber is separated from the first chamber by a fluid-tight seal;

a pressure transducer means secured in the first chamber in a depression on the electrically insulated intervening wall, which pressure transducer means is exposed to the first chamber for sensing and converting fluid pressure exhibited by a fluid in the first chamber into electrical impulses;

an electrically nonconductive, fluid pressure responsive media covering the pressure transducer means which separates the pressure transducer means from direct contact with fluid present in the first chamber;

electrical conducting means connected to the pressure transducer means for transmitting and receiving electrical impulses from the pressure transducer means and which extends through the intervening wall into the second chamber to provide a pathway for electricity between the pressure transducer means in the first chamber and the second chamber; and receptor means on the housing for receiving and connecting the housing to electrical wiring means for powering the pressure transducer means and for transferring electrical impulses generated by the pressure transducer means and corresponding to determined pressures.

22. A disposable pressure transducer assembly as recited in claim 21 wherein the electrically nonconductive fluid pressure responsive media comprises silicone elastomer.

23. A disposable pressure transducer assembly as recited in claim [20] *21* further comprising tubing connecting means on the inlet and outlet ports for connecting tubing to the housing.

24. A disposable pressure transducer assembly as recited in claim 21 wherein the electrical conducting means comprises a plurality of electrical conducting metal pins electrically interconnected to the pressure transducer means to transfer power to the pressure transducer means and to transfer away electric impulse signals corresponding to determined pressures.

25. A disposable pressure transducer assembly as recited in claim 21 wherein the electrically insulated intervening wall within the chamber comprises a polysulfone wall.

26. A disposable pressure transducer assembly as recited in claim 21 wherein the pressure transducer means comprises a monolithic silicon pressure sensor employing a four-terminal resistive element formed in a monocrystalline silicon diaphragm.

27. A disposable pressure transducer assembly as recited in claim 21 wherein the pressure transducer means monitors fluid pressure within the first chamber in the range from about −50 mmHg to +300 mmHg.

28. A disposable pressure transducer assembly as recited in claim 21 further comprising a clear lens means on the housing extending over the first chamber for viewing fluid and bubbles in the fluid within the first chamber.

29. A disposable pressure transducer assembly as recited in claim 28 wherein the clear lens means comprises a clear dome portion on the housing extending over at least a portion of the first chamber.

30. A disposable pressure transducer assembly as recited in claim 21 wherein the housing comprises a biocompatible polymeric material.

31. A disposable pressure transducer assembly as recited in claim 30 wherein the biocompatible polymeric material is selected from the group consisting of polycarbonate, polypropylene, polyethylene and polysulfone.

32. A disposable pressure transducer assembly as recited in claim 21 further comprising vent means on the housing and on the electrically insulated intervening wall for providing exposure to the atmosphere for the pressure transducer means.

33. A disposable pressure transducer assembly as recited in claim 32 wherein the vent means comprises an opening extending through the housing into the second chamber and aligned with an opening extending through the electrically insulated intervening wall and leading to the pressure transducer means.

34. A disposable pressure transducer assembly as recited in claim 21 further comprising a wiring connector means which engages the electrical conducting means in the second chamber for transmitting electrical impulses generated by the pressure transducer means along electrical wiring to a monitoring means for displaying fluid pressure in fluid in the first chamber.

35. A disposable pressure transducer assembly as recited in claim 34 wherein the electrical conducting means comprises electrical pins extending into the second chamber and the wiring connector means comprises a body having electrical pins engaging terminals and which slides into the second chamber and which [engaging] *engages* the electrical pins.

36. A disposable pressure transducer assembly as recited in claim 21 wherein the pressure transducer means includes a temperature compensation circuit means for determining fluid pressure at the sensed temperature of a fluid in the first chamber.

37. A disposable pressure transducer assembly as recited in claim 21 wherein the inlet port and outlet are *port* axially aligned.

38. A disposable pressure transducer assembly for invasively monitoring blood pressure comprising:

a housing comprised of polysulfone defining a chamber therewithin, having an inlet port and an outlet port in fluid-flow communication with the chamber and having a first aperture opening to the chamber;

an electrically insulated intervening wall in the chamber comprised of polysulfone which separates the chamber into a first chamber and a second chamber wherein the first chamber is in fluid-flow communication with the inlet port and outlet port and the second chamber having an opening through the housing and separated from the first chamber by a fluid-tight seal and the first aperture extends into the second chamber and aligns with a second aperture extending through the electrically insulated intervening wall;

a pressure transducer means secured in the first chamber in a depression on the electrically insulated intervening wall, which pressure transducer means is exposed to the first chamber for sensing and converting fluid pressure exhibited by a fluid in the first chamber into electrical impulses;

an electrically nonconductive fluid pressure responsive media comprising silicone elastomer covering the pressure transducer means which separates the pressure transducer means from direct contact with fluid present in the first chamber;

electrical conducting pins connected to the pressure transducer means for transmitting and receiving electrical impulses from the pressure transducer means and which extend through the intervening wall into the second chamber to provide a pathway for electricity between the pressure transducer means in the first chamber and the second chamber; and snap-fitting resilient arms on the housing which combine with the opening through the housing into the second chamber which receives and connects the housing to electrical wiring means for powering the pressure transducer means and for transferring electrical impulses generated by the pressure transducer means and corresponding to determined pressures.

39. A disposable pressure transducer assembly as recited in claim 38 wherein the pressure transducer means comprises a monolithic silicon pressure sensor employing a four-terminal resistive element formed in a monocrystalline silicon diaphragm.

40. A disposable pressure transducer assembly as recited in claim 38 wherein the pressure transducer means monitors fluid pressure within the first chamber in the range from about −50 mmHg to +300 mmHg.

41. A disposable pressure transducer assembly as recited in claim 38 wherein the pressure transducer means includes a temperature compensation circuit means for determining fluid pressure at the sensed temperature of a fluid in the first chamber.

42. A disposable pressure transducer assembly as recited in claim 38 further comprising a clear lens means on the housing extending over the first chamber for viewing fluid and bubbles in the fluid within the first chamber.

43. A disposable pressure transducer assembly as recited in claim 42 wherein the clear lens means comprises a clear dome portion on the housing extending over at least a portion of the first chamber.

44. A disposable pressure transducer assembly as recited in claim 38 wherein the inlet [por] *port* and outlet port are axially aligned.

45. A disposable pressure transducer assembly for invasively monitoring blood pressure comprising:

a housing comprised of polysulfone with at least a portion of the housing forming a dome and extending over and defining a chamber with the housing, the housing including an inlet port and an outlet port in fluid-flow communication with the chamber and a first aperture opening to the chamber;

an electrically insulated intervening wall in the chamber comprised of polysulfone which separates the chamber into a first chamber and a second chamber wherein the first chamber is in fluid-flow communication with the inlet port and outlet port and the second chamber having an opening through the housing and separated from the first chamber by a fluid-tight seal and the first aperture extends into the second chamber and aligns with a second aperture extending through the electrically insulated intervening wall;

a pressure transducer means secured in the first chamber in a depression on the electrically insulated intervening wall, which pressure transducer means is exposed to the first chamber for sensing and converting fluid pressure exhibited by a fluid in the first chamber into electrical impulses;

an electrically nonconductive fluid pressure responsive media comprising silicone elastomer covering the pressure transducer means which separates the pressure transducer means from direct contact with fluid present in the first chamber.

electrical conducting pins connected to the pressure transducer means for transmitting and receiving electrical impulses from the pressure transducer means and which extend through the intervening wall into the second chamber to provide a pathway for electricity between the pressure transducer means in the first chamber and the second chamber; and snap-fitting resilient arms on the housing which combine with the opening through the housing into the second chamber which receives and connects the housing to electrical wiring means for powering the pressure transducer means and for transferring electrical impulses generated by the pressure transducer means and corresponding to determined pressures.

46. A disposable pressure transducer assembly as recited in claim 45 wherein the pressure transducer means comprises a monolithic silicon pressure sensor employing a four-terminal resistive element formed in a monocrystalline silicon diaphragm.

47. A disposable pressure transducer assembly as recited in claim 45 wherein the pressure transducer means monitors fluid pressure within the first chamber in the range from about −50 mmHg to +300 mmHg.

48. A disposable pressure transducer assembly as recited in claim 45 wherein the pressure transducer means includes a temperature compensation circuit means for determining fluid pressure at the sensed temperature of a fluid in the first chamber.

49. A disposable pressure transducer assembly as recited in claim 45 wherein the inlet port and outlet port are axially aligned.

50. A pressure transducer assembly for monitoring pressure in a fluid comprising:

a housing defining a chamber and having an inlet port and an outlet port in fluid-flow communication with the chamber;

an insulated body sealed within the chamber which forms separate first and second chambers within the housing with the first chamber in fluid-flow communication with the inlet port and outlet port and adapted to be filled with fluid from the inlet port;

a pressure transducer means secured on the insulated body and exposed to pressure of fluid in the first chamber for determining and converting fluid pressure within a fluid adapted to be in the first chamber into electrical impulses;

temperature compensation means for compensating the sensed pressure in the fluid based upon the temperature of the fluid and correcting such sensed pressure;

a fluid pressure responsive media which is electrically nonconductive and which separates the pressure transducer means from any fluid present in the first chamber; and an electrical conductor connected to the pressure transducer means.

51. A pressure transducer as described in claim 50 wherein the insulating body has an opening extending between the first and second chambers, said pressure transducer means is in communication with said opening and said fluid pressure responsive media is in said opening.

52. A pressure transducer as described in claim 51 wherein the fluid pressure responsive media is a polymeric material and the transducer is aligned with the opening.

53. A pressure transducer assembly for monitoring pressure in a fluid comprising:

a housing having an inlet port and an outlet port;

means for forming a partition within the housing to provide separate first and second chambers within the housing with the first chamber in fluid-flow communication with the inlet port and outlet port and adapted to be filled with fluid from the inlet port, said housing having a portion through which fluid in the first chamber can be observed;

a pressure transducer carried by the partition and exposed to pressure of fluid in the first chamber for determining and converting fluid pressure within a fluid adapted to be in the first chamber into electrical impulses;

a fluid pressure responsive media which is electrically nonconductive and which separates the pressure transducer from any fluid present in the first chamber; and an electrical conductor connected to the pressure transducer and extending from the pressure transducer.

54. A pressure transducer assembly for monitoring pressure in a fluid comprising:

a biocompatible housing having an inlet port and an outlet port;

means for forming a partition within the housing to provide separate first and second chambers within the housing with the first chamber in fluid-flow communication with the inlet port and outlet port, said housing having a portion through which fluid in the first chamber can be observed;

said partition having an opening extending between the first and second chambers;

a pressure transducer for sensing pressure of the fluid;

temperature compensation means for compensating the sensed pressure in the fluid based upon the temperature of the fluid and correcting such sensed pressure;

means for mounting the pressure transducer in said housing in communication with said opening whereby the pressure transducer is exposed to pressure of fluid adapted to be in the first chamber for determining and converting fluid pressure within a fluid in the first chamber into electrical impulses;

a biocompatible electrically nonconductive fluid pressure responsive media in said opening for separating the pressure transducer from any fluid present in the first chamber; and an electrical conductor connected to the pressure transducer.

55. A pressure transducer as described in claim 54 wherein said partition is a nonconductor of electricity between the first and second chambers.

56. A pressure transducer as described in claim 54 wherein the transducer is aligned with said opening and supported by the partition.

57. A pressure transducer assembly for monitoring pressure in a fluid comprising:

a housing having an inlet port and an outlet port;

a source of I.V. solution;

flexible tubing connected to the source of I.V. solution and to the inlet port;

means for coupling the outlet port to the patient;

means for forming a partition within the housing to provide separate first and second chambers within the housing with the first chamber in fluid-flow communication with the inlet port and outlet port and adapted to be filled with fluid from the inlet port, said housing having a portion through which fluid in the first chamber can be observed;

a pressure transducer carried by the partition and exposed to pressure of fluid in the first chamber for determining and converting fluid pressure within a fluid adapted to be in the first chamber into electrical impulses;

a fluid pressure responsive media which is electrically nonconductive and which separates the pressure transducer from any fluid present in the first chamber; and an electrical conductor connected to the pressure transducer and extending from the pressure transducer.

58. A pressure transducer assembly for monitoring pressure in a fluid comprising:

a biocompatible housing having an inlet port and an outlet port;

means for forming a partition within the housing to provide separate first and second chambers within the housing with the first chamber in fluid-flow communication with the inlet port and outlet port and adapted to be filled with fluid from the inlet port;

a pressure transducer carried by the partition and exposed to pressure of fluid in the first chamber for determining and converting fluid pressure within a fluid adapted to be in the first chamber into electrical impulses;

a biocompatible fluid pressure responsive media which is electrically nonconductive and which separates the pressure transducer from any fluid present in the first chamber; and an electrical conductor connected to the pressure transducer and extending from the pressure transducer.

* * * * *

UNITED STATES PATENT AND TRADEMARK OFFICE

CERTIFICATE OF CORRECTION

PATENT NO. : Re. 33,518

DATED : Jan. 15, 1991

INVENTOR(S) : Kenneth R. McCord et al

It is certified that error appears in the above-identified patent and that said Letters Patent is hereby corrected as shown below:

Column 1, line 18 change "monitoring as" to -- monitoring is --.

Column 2, line 26 after "current" insert -- cannot --.

Column 3, line 58 after "any" insert -- air --.

Column 5, line 58 change "of flexible" to -- to flexible --.

Column 6, line 12 after "56" insert -- which --.

Column 6, line 62 change "required" to -- recited --.

Column 8, line 19 after "chamber" change the period to a semicolon.

Column 9, lines 60-61 change "are port" to -- port are --.

Column 11, line 1 change "with" to -- within --.

Column 11, line 27 after "chamber" change the period to a semicolon.

Signed and Sealed this

Thirteenth Day of October, 1992

*Attest:*

DOUGLAS B. COMER

*Attesting Officer*

*Acting Commissioner of Patents and Trademarks*